United States Patent [19]

Aoyama et al.

[11] Patent Number: 4,810,642
[45] Date of Patent: Mar. 7, 1989

[54] METHOD AND TEST COMPOSITION FOR DETERMINATION OF HYDROGEN PEROXIDE

[75] Inventors: Norihito Aoyama, Shizuoka; Mikio Okano, Nagoya; Akira Miike, Shizuoka; Toshio Tatano, Numazu, all of Japan

[73] Assignee: Kyowa Medex Co., Ltd., Tokyo, Japan

[21] Appl. No.: 878,207

[22] Filed: Jun. 25, 1986

[30] Foreign Application Priority Data

Jun. 26, 1985 [JP] Japan ................. 60-139350

[51] Int. Cl.⁴ ................. C12Q 1/28; G01N 31/22
[52] U.S. Cl. ................. 435/28; 436/66; 436/135; 436/904
[58] Field of Search ............ 435/28; 436/66, 135, 436/904

[56] References Cited

U.S. PATENT DOCUMENTS 4,587,100  5/1986  Amano et al. ............ 422/60 X

FOREIGN PATENT DOCUMENTS

| 0024578 | 3/1981  | European Pat. Off. |
| 0029104 | 5/1981  | European Pat. Off. |
| 0057661 | 8/1982  | European Pat. Off. |
| 0105443 | 4/1984  | European Pat. Off. |
| 0108526 | 5/1984  | European Pat. Off. |
| 0120399 | 10/1984 | European Pat. Off. |
| 0121254 | 10/1984 | European Pat. Off. |
| 0124287 | 11/1984 | European Pat. Off. |
| 0124909 | 11/1984 | European Pat. Off. |
| 0153872 | 9/1985  | European Pat. Off. |
| 56-31641 | 3/1981 | Japan. |
| 60-83598 | 5/1985 | Japan. |

OTHER PUBLICATIONS

Chem. Abs., vol. 90, No. 23, (1979), 182296q.
Chem. Abs., vol. 98, No. 17, (1983), 139879k.

*Primary Examiner*—Barry S. Richman
*Assistant Examiner*—Jill Johnston
*Attorney, Agent, or Firm*—Fitzpatrick, Cella, Harper & Scinto

[57] ABSTRACT

A method and test composition for colorimetrically determining hydrogen peroxide in a sample includes a chromogen of the formula:

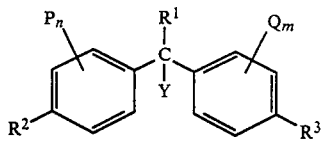

which is reacted with hydrogen peroxide in the sample in the presence of peroxidase. The absorbancy of the reaction solution is then measured.

16 Claims, No Drawings

METHOD AND TEST COMPOSITION FOR DETERMINATION OF HYDROGEN PEROXIDE

BACKGROUND OF THE INVENTION

The present invention relates to a method and test composition for the determination of hydrogen peroxide, and more particularly, to a method for the determination of hydrogen peroxide by reacting hydrogen peroxide with a novel chromogen as a hydrogen donor in the presence of peroxidase and determining the degree of pigment formed. The invention also pertains to a test composition suitable for carrying out such determination.

Heretofore, the determination of a substrate is generally carried out by oxidizing the substrate by the action of oxidase and determining the formed hydrogen peroxide. For example, cholesterol is oxidized by cholesterol oxidase to form hydrogen peroxide. The hydrogen peroxide is then determined by reacting the hydrogen peroxide with a chromogen in the presence of peroxidase to form a pigment and measuring the absorbancy of the reaction solution colored by the formation of the pigment in the visible ray region. In such processes, 4-amino-antipyrine (hereinafter referred to as "4AA") and phenol, 4AA and N,N-dimethylaniline, 4AA and N-ethyl-N-($\beta$-hydroxyethyl)-m-toluidine, 3-methylbenzothiazolin hydrazone and N,N-diethylaniline, 4AA and N-ethyl-N-(3-methylphenyl)-N'-acetylethylenediamine (hereinafter referred to as "EMAE") and the like are generally used as the chromogen.

The pigments formed by using these chromogens lacks stability under alkaline sides beyond pH 7.0.

On the other hand, the optimum pH of many enzymes used for diagnostic purposes is on the alkaline side.

Therefore, there is a need to develop chromogens which are superior in sensitivity, and stable on the alkaline side.

SUMMARY OF THE INVENTION

It has now been found that a compound represented by the following formula (I) or salt thereof is excellent as a chromogen.

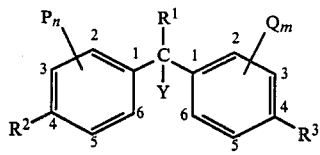

In the above formula, Y is hydrogen or hydroxyl; $R^1$ is a group represented by the general formula (II) or (III)

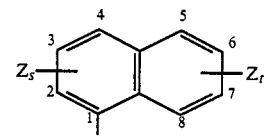

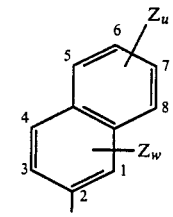

wherein Z is hydroxyl, alkyl, sulfo or carboxyl, s, t, u and w is 0 or an integer of 1 to 3, and each Z in $Z_s$, each Z in $Z_t$, each Z in $Z_u$ and each Z in $Z_w$ are the same or different, P and Q are hydroxyl, alkyl, sulfo or carboxyl; n and m is 0 or an integer of 1 to 3; each P in $P_n$ and each Q in $Q_m$ are the same or different and $R^2$ and $R^3$ may be the same or different and are hydroxyl, amino or substituted amino.

In the foregoing definitions, the substituent in the substituted amino for $R^2$ and $R^3$ is exemplified by alkyl, sulfoalkyl, etc. As used herein, alkyl includes alkyl groups having 1 to 5 carbon atoms such as methyl, ethyl, propyl, butyl, pentyl, etc.

The salt include a salt with acid such as sulfuric acid, phosphoric acid, hydrochloride and an alkali metal salt such as sodium salt, potassium salt, etc.

Compounds represented by the formula (I) [hereinafter referred to as chromogen (A)] are chromogens known as an intermediate for dye synthesis, and most of them are synthesized by condensation reaction of Michler's hydrol with a naphthalene derivative or by reduction reaction of a commercially available pigment.

In accordance with the present invention, hydrogen peroxide in a sample is determined by reacting chromogen (A) with hydrogen peroxide and measuring the absorbancy of the reaction solution colored by formation of a pigment at a maximum absorption wavelength of the pigment ($\lambda_{max}$) in the visible ray region.

The principle of the present invention is on the basis of the fact that the reaction of hydrogen peroxide in a sample with the chromogen proceeds stoichiometrically in the presence of peroxidase to form a pigment and the amount of formed pigment is proportional to the amount of formed hydrogen peroxide.

DESCRIPTION OF THE INVENTION

Representative examples of chromogens used in the present invention are shown in Table 1, wherein the symbols in the Table show the following groups and the number in parenthesis shows the position of substituent groups.

M: $CH_3$
E: $C_2H_5$
D: $CH_2CH_2CH_2SO_3H$

TABLE 1

| No. | Y  | $R^1$ | $R^2$  | $R^3$  | $Z_s$, $Z_t$, $Z_u$ or $Z_w$ |        | $P_n$  | $Q_m$  |
|-----|----|----|--------|--------|---------|--------|--------|--------|
| 1   | H  | II | $NM_2$ | $NM_2$ | OH (2)  |        |        |        |
| 2   | OH | "  | "      | "      | "       |        |        |        |
| 3   | H  | "  | "      | "      | "       | OH (7) |        |        |
| 4   | OH | "  | "      | "      | "       | "      |        |        |
| 5   | H  | "  | "      | "      | OH (3)  | OH (6) |        |        |

TABLE 1-continued

| No. | Y | $R^1$ | $R^2$ | $R^3$ | $Z_s, Z_t, Z$ or $Z_w$ | | | $P_n$ | | $Q_m$ | |
|---|---|---|---|---|---|---|---|---|---|---|---|
| 6 | OH | " | " | " | " | " | | | | | |
| 7 | H | III | " | " | " | " | | | | | |
| 8 | OH | " | " | " | " | " | | | | | |
| 9 | H | " | " | " | OH (1) | OH (5) | | | | | |
| 10 | OH | " | " | " | " | " | | | | | |
| 11 | H | II | " | " | OH (2) | $SO_3H$ (6) | | | | | |
| 12 | OH | " | " | " | " | " | | | | | |
| 13 | H | " | " | " | " | $SO_3H$ (7) | | | | | |
| 14 | OH | " | " | " | " | " | | | | | |
| 15 | H | " | " | " | " | $SO_3H$ (8) | | | | | |
| 16 | OH | " | " | " | " | " | | | | | |
| 17 | H | " | " | " | " | $SO_3H$ (3) | | | | | |
| 18 | OH | " | " | " | " | " | | | | | |
| 19 | H | III | " | " | OH (1) | " | | | | | |
| 20 | OH | " | " | " | " | " | | | | | |
| 21 | H | " | " | " | " | $SO_3H$ (4) | | | | | |
| 22 | OH | " | " | " | " | " | | | | | |
| 23 | H | II | " | " | OH (2) | OH (3) | $SO_3H$ (6) | | | | |
| 24 | OH | " | " | " | " | " | " | | | | |
| 25 | H | " | " | " | " | $SO_3H$ (3) | OH (7) | | | | |
| 26 | OH | " | " | " | " | " | " | | | | |
| 27 | H | " | " | " | " | " | $SO_3H$ (6) | | | | |
| 28 | OH | " | " | " | " | " | " | | | | |
| 29 | H | III | " | " | OH (1) | " | " | | | | |
| 30 | OH | " | " | " | " | " | " | | | | |
| 31 | H | II | " | " | OH (2) | COOH (3) | " | | | | |
| 32 | OH | " | " | " | " | " | " | | | | |
| 33 | H | " | OH | OH | " | $SO_3H$ (3) | $SO_3H$ (6) | COOH (3) | $CH_3$(5) | COOH (3) | $CH_3$(5) |
| 34 | OH | " | " | " | " | " | " | " | " | " | " |
| 35 | H | " | $NE_2$ | $NE_2$ | $SO_3H$ (3) | $SO_3H$ (6) | | | | | |
| 36 | OH | " | " | " | " | " | | | | | |
| 37 | H | " | $NH_2$ | $NH_2$ | OH (2) | $SO_3H$ (3) | $SO_3H$ (6) | | | | |
| 38 | OH | " | " | " | " | " | " | | | | |
| 39 | H | " | NHD | NHD | " | " | " | | | | |
| 40 | OH | " | " | " | " | " | " | | | | |

Comparative tests between the chromogens indicated in Table 1 and known compounds in respect of maximum absorption wavelength ($\lambda_{max}$), sensitivity and degree of color development in reagent blank are conducted according to the following method.

Good's buffer [a generic term for buffers containing compounds such as, for example, N-(2-acetamido)-2-aminoethanesulfonic acid and the like sold by the Sigma Corporation] solution (pH 7.5) containing 10 U/ml peroxidase, 1 mg/ml Triton X-100 ®, a polyethylene gylcol mono-p-iso-octylphenyl ether, also sold by the Sigma Corporation and 0.2 mg/ml chromogen (A) is prepared as reagent solution. To 20 μl of 10.33 mg/dl $H_2O_2$ solution is added 3 ml of the reagent solution and the mixture is subjected to reaction. The OD value of the reaction solution at $\lambda_{max}$ is measured.

The sensitivity is shown defining the OD value obtained by using (4AA-EMAE) as 100.

The degree of the color development in reagent blank is shown as compared with degree of color development with the elapse of time of the reagent solution obtained by using Leuco Bindschedler's Green (LBG). "AA" means that the degree of color development is much lower than that of LBG. "A" means that it is lower, and "B" means that it is equal to that of LBG.

As the sensitivity is higher and the degree of color development in reagent blank is lower, the chromogen as hydrogen donor is better and the trace amount of the component is suitably determined by using the chromogen.

The results are shown in Table 2.

TABLE 2

| Compound No. | $\lambda_{max}$ (nm) | Sensitivity | Color Development in Reagent Blank |
|---|---|---|---|
| 1 | 634 | 1850 | AA |
| 2 | 634 | 1850 | AA |
| 3 | 630 | 1820 | AA |
| 4 | 630 | 1820 | AA |
| 5 | 610 | 430 | AA |
| 6 | 610 | 430 | AA |
| 7 | 630 | 420 | AA |
| 8 | 630 | 420 | AA |
| 9 | 620 | 560 | AA |
| 10 | 620 | 560 | AA |
| 11 | 631 | 450 | AA |
| 12 | 631 | 450 | AA |
| 13 | 630 | 1330 | AA |
| 14 | 630 | 1330 | AA |
| 15 | 630 | 1350 | AA |
| 16 | 630 | 1350 | AA |
| 17 | 630 | 280 | AA |
| 18 | 630 | 280 | AA |
| 19 | 615 | 150 | AA |
| 20 | 615 | 150 | AA |
| 21 | 604 | 80 | AA |
| 22 | 604 | 80 | AA |
| 23 | 625 | 415 | AA |
| 24 | 625 | 415 | AA |
| 25 | 630 | 530 | AA |
| 26 | 630 | 530 | AA |
| 27 | 620 | 2080 | A |
| 28 | 620 | 2080 | A |
| 29 | 630 | 940 | AA |
| 30 | 630 | 940 | AA |
| 31 | 633 | 950 | AA |
| 32 | 633 | 950 | AA |
| 33 | 550 | 320 | AA |
| 34 | 550 | 320 | AA |
| 35 | 640 | 390 | AA |
| 36 | 640 | 390 | AA |
| 37 | 580 | 670 | A |
| 38 | 580 | 670 | A |
| 39 | 610 | 1800 | A |

TABLE 2-continued

| Compound No. | $\lambda_{max}$ (nm) | Sensitivity | Color Development in Reagent Blank |
|---|---|---|---|
| 40 | 610 | 1800 | A |
| 4AA-EMAE | 555 | 100 | AA |
| LBG | 728 | 410 | B |

In carrying out the present invention, the chromogen (A) and peroxidase are dissolved in a buffer solution to prepare a reagent solution. The reagent solution are added to a sample containing hydrogen peroxide or to the system where hydrogen peroxide is produced (hereinafter referred to as "$H_2O_2$—producing system"). The absorbancy of the reaction solution colored by the formation of a pigment is measured at a maximum absorption wavelength of the formed pigment in the visible ray region, 500–800 nm. On the other hand, the standard curve showing the relation between the amount of hydrogen peroxide and absorbancy is separately prepared by using a standard hydrogen peroxide solution as the sample. The amount of hydrogen peroxide in the sample is calculated by applying the obtained absorbancy to the standard curve.

The reaction is usually carried out at a temperature of 5°–50° C., preferably 25°–40° C. in a buffer solution having a pH of 2–11 and is completed in several minutes.

The chromogen is used in an equimolar amount with hydrogen peroxide or more, preferably 10–1000 mole equivalents. Peroxidase is used in a concentration of 0.1–1000 IU/ml.

As buffers, Good's buffer, phosphate buffer, tris-HCl buffer, succinate buffer, oxalate buffer, citrate buffer, acetate buffer, etc. may be used in a concentration of 0.005–2 mol/l.

In the reaction, a surfactant such as Triton X-100 ®, etc. is used, if required to clear the solution of turbidity.

As is described later, the present method can be applied to the determination of a substrate or enzyme activity taking part in the $H_2O_2$-producing system.

Particularly, when the system is an enzymatic reaction, both the $H_2O_2$-producing system and the system where pigment is produced [hereinafter referred to as pigment-producing system] proceed at the same time in the same system and therefore, such a method is simple and convenient.

The factors to be determined include, for example a substrate such as uric acid, cholesterol, triglyceride, fatty acid, sialic acid, pyruvic acid, glucose, inorganic phosphorus, phospholipid, monoamine, o-toruoylcholine, creatine, sarcosine and polyamine, and an enzyme such as monoamine oxidase and choline esterase.

The substrates or enzymes of these enzymatic reactions are contained in serum, urea, etc. and the determination of the substrates is useful for diagnostic purposes.

When the factor to be determined is a substrate, an enzyme which decomposes the substrate to form hydrogen peroxide is added with a chromogen to the reagent solution; when the factor is an enzyme activity, a substrate for the enzyme is added. The reagent solution is added to a sample, and a reaction is carried out to form a pigment.

When the factor to be determined is a substrate, the reaction is generally carried out for about 5 to 10 minutes before the absorption measurement, and the desired factor can be determined by colorimetrically measuring the absorption of the reaction solution. When the factor is an enzyme activity, a rate of pigment formation at an appropriate time after the start of reaction is generally determined from changes in the absorbance of reaction solution, whereby the activity can be determined.

Examples of enzymatic reaction are schematically shown as follows.

1. Uric acid

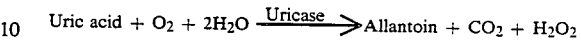

2. Total choresterol

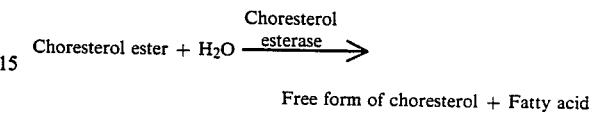

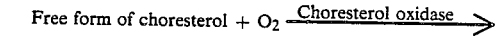

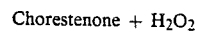

3. Triglyceride

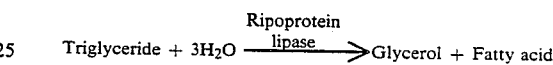

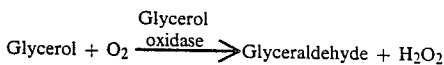

4. Free form of fatty acid

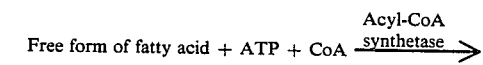

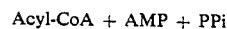

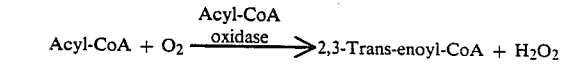

5. Sialic acid

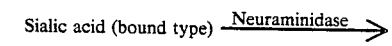

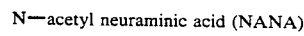

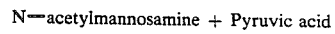

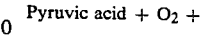

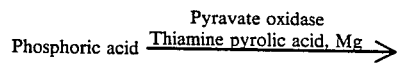

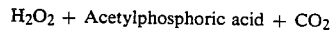

6. Pyruvic acid

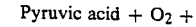

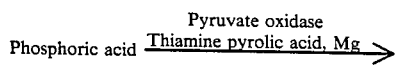

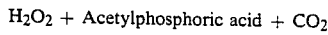

7. Glucose

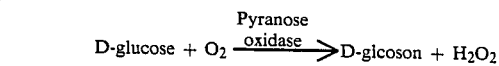

8. Inorganic phosphorus

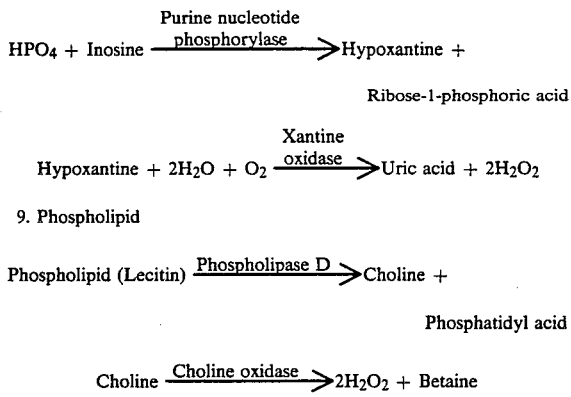

9. Phospholipid

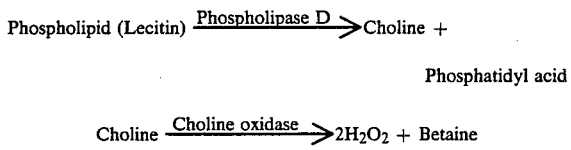

10. Monoamine oxidase

Monoamines (substrate) + H$_2$O $\xrightarrow{\text{Monoamine oxidase}}$ (Acrolein) + NH$_3$ + H$_2$O$_2$

11. Choline esterase

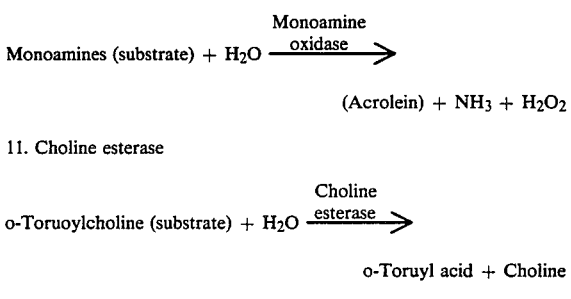

12. Creatine

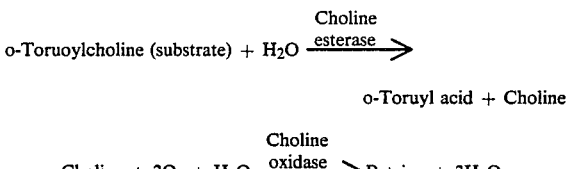

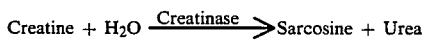

13. Polyamine (Putrescine)

Putrescine + O$_2$ + H$_2$O $\xrightarrow{\text{Putrescine oxidase}}$

γ-Aminobutylaldehyde + NH$_3$ + H$_2$O$_2$

The hydrogen peroxide-producing reaction and pigment-producing reaction may be conducted stepwise or preferably, the determination of hydrogen peroxide is performed by adding to the sample the components necessary for the determination of hydrogen peroxide conducting all the reactions in one step and measuring the absorbancy of the reaction solution.

The components comprises oxidase for the substrate to be determined, peroxidase and chromogen (A). A buffer solution and surfactant, etc. may be added, if necessary. Of course, if components for oxidizing the substrate in addition to oxidase for the substrate are required, such components must be added to the H$_2$O$_2$-producing system.

Another aspect of the present invention is to provide a test composition for the determination of hydrogen peroxide which comprises oxidase for the substrate to be determined, the chromogen represented by the formula (I) and peroxidase. The composition may also contain a buffer reagent as well as surfactants such as polyoxyethylenealkylether, antiseptics such as sodium azide, ascorbate oxidase for decomposing ascorbic acid, etc., if necessary. Further the composition may contain components necessary for producing hydrogen peroxide other than oxidase for the substrate.

Certain specific embodiments of the invention are illustrated by the following representative examples.

EXAMPLE 1 (DETERMINATION OF URIC ACID)

In this example, 10 U of uricase, 1000 U of peroxidase, 100 mg of Triton X-100 ® and 10 mg of (A) Compound No. 1, (B) Compound No. 3, (C) Compound No. 13, (D) Compound No. 15, (E) Compound No. 25, (F) Compound No. 27, (G) Compound No. 29, (H) Compound No. 31, (I) Compound No. 37 or (J) Compound No. 39 as a chromogen are dissolved in 100 ml of 50 mM Good's buffer solution (pH 8.0) to prepare a reagent solution. To a test tube are poured 10 ml of serum and 3 ml of the reagent solution, and the mixture is incubated for reaction at 37° C. for 10 minutes.

The absorbancy of the reaction solution at λ$_{max}$ is measured using reagent blank as a control. The concentration of uric acid in the serum is calculated by using calibration curve prepared in advance.

For comparison, the same test sample is analyzed by the ultra violet spectrophotometric method of uricase. The results are shown in Table 3.

TABLE 3

| Serum No. | Uric acid content (mg/dl) | | | | | | | | | |
|---|---|---|---|---|---|---|---|---|---|---|
| | Control | A | B | C | D | E | F | G | H | I | J |
| 1 | 4.1 | 4.1 | 4.0 | 4.1 | 3.9 | 4.2 | 4.1 | 4.2 | 4.2 | 4.0 | 4.0 |
| 2 | 2.9 | 2.8 | 2.8 | 2.8 | 2.9 | 2.8 | 2.9 | 3.0 | 2.8 | 2.9 | 2.8 |
| 3 | 5.6 | 5.5 | 5.6 | 5.5 | 5.5 | 5.7 | 5.6 | 5.6 | 5.6 | 5.6 | 5.6 |
| 4 | 1.4 | 1.4 | 1.3 | 1.3 | 1.5 | 1.4 | 1.4 | 1.5 | 1.5 | 1.4 | 1.4 |
| 5 | 10.8 | 10.6 | 10.8 | 10.6 | 10.9 | 10.7 | 10.6 | 10.8 | 10.8 | 10.6 | 10.7 |

EXAMPLE 2 (DETERMINATION OF CREATINE)

In this example, 500 U of peroxidase, 1000 U of sarcosine oxidase, 4500 U of creatinase, 200 mg of Triton X-100 ® and 10 mg of (A) Compound No. 1, (B) Compound No. 3, (C) Compound No. 13, (D) Compound No. 15, (E) Compound No. 25, (F) Compound No. 27, (G) Compound No. 29, (H) Compound No. 31, (I) Compound No. 37 or (J) Compound No. 39 as a chromogen are dissolved in 100 ml of 0.1M Tris-HCl buffer solution (pH 7.5) to prepare a reagent solution. To a test tube are poured 50 μl of serum and 3 ml of the reagent solution and the mixture is incubated for reaction at 37° C. for 10 minutes.

The absorbancy of the reaction solution at λ$_{max}$ is measured using reagent blank as a control. The concentration of creatine in serum is calculated by using calibration curve prepared in advance.

For comparison, after creatinine and ammonia in serum are decomposed in advance, creatine is converted into creatinine, and the sample is exposed to the actions of creatinine deminase and glutamic acid dehydrogenase. Creatine is determined from the change in the absorbancy of NADPH in 340 nm. The results are shown in Table 4.

TABLE 4

| Serum No. | Creatine content (mg/dl) | | | | | | | | | |
|---|---|---|---|---|---|---|---|---|---|---|
| | Control | A | B | C | D | E | F | G | H | I | J |
| 1 | 0.36 | 0.36 | 0.37 | 0.36 | 0.36 | 0.35 | 0.34 | 0.37 | 0.36 | 0.34 | 0.38 |
| 2 | 0.49 | 0.51 | 0.51 | 0.49 | 0.50 | 0.49 | 0.51 | 0.47 | 0.49 | 0.49 | 0.49 |
| 3 | 1.15 | 1.12 | 1.14 | 1.12 | 1.15 | 1.16 | 1.15 | 1.12 | 1.14 | 1.16 | 1.16 |
| 4 | 0.28 | 0.28 | 0.26 | 0.30 | 0.30 | 0.27 | 0.27 | 0.28 | 0.28 | 0.29 | 0.29 |
| 5 | 0.73 | 0.75 | 0.75 | 0.71 | 0.73 | 0.71 | 0.74 | 0.73 | 0.73 | 0.73 | 0.72 |

As is apparent from the results obtained in Examples 1 and 2, trace components in a slight amount of a test sample such as serum can be determined with accuracy.

What is claimed is:

1. A method for the determination of hydrogen peroxide which comprises reacting a chromogen represented by the general formula (I)

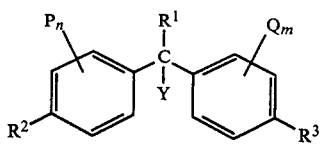

wherein Y is hydrogen or hydroxyl; $R^1$ is a group represented by the general formula (II) or (III)

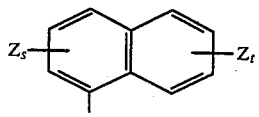

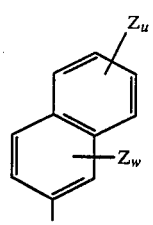

wherein Z is hydroxyl, alkyl or carboxyl; s, t, u and w is 0 or an integer of 1 to 3; and each Z in $Z_s$, each Z in $Z_t$, each Z in $Z_u$ and each Z in $Z_w$ are the same or different, P and Q are hydroxyl, alkyl, sulfo or carboxyl; n and m is 0 or an integer of 1 to 3; each P in $P_n$ and each Q in $Q_m$ are the same or different and $R^2$ and $R^3$ may be the same or different and are hydroxyl, amino or substituted amino or salt thereof, with hydrogen peroxide in the presence of peroxidase; and measuring the absorbancy of the reaction solution colored by formation of a pigment in the visible ray region.

2. A method according to claim 1, wherein said reaction is carried out in an alkaline solution.

3. A method according to claim 1, wherein said $R^2$ and $R^3$ are dimethylamino group.

4. A method according to claim 1, wherein said reaction is carried out in a buffer solution.

5. A method according to claim 4, wherein said buffer is selected from the group consisting of phosphate, Tris-hydrochloride, succinate, oxalate, citrate, acetate and Good's.

6. A method according to claim 1, wherein said reaction is carried out in the presence of surfactant.

7. A method according to claim 6, wherein said surfactant is polyethylene gylcol mono-p-iso-octylphenyl ether.

8. A method according to claim 1, wherein said hydrogen peroxide is a product formed by enzymatic reaction.

9. A method according to claim 8, wherein said hydrogen peroxide-producing reaction and the reaction of hydrogen peroxide with said chromogen are conducted simultaneously.

10. A method according to claim 8, wherein said enzymatic reaction is the oxidation of a substrate using oxidase.

11. A method according to claim 10, wherein said oxidase is selected from the group consisting of uricase, cholesterol oxidase, xanthin oxidase, choline oxidase, pyruvate oxidase, glicerin-3-phosphate oxidase, acyl CoA oxidase, glycerol oxidase, glucose oxidase, pyranose oxidase, sarcosine oxidase, putrescine oxidase and galactose oxidase.

12. A test composition for the determination of hydrogen peroxide which comprises the chromogen defined in claim 1 and peroxidase.

13. A test composition according to claim 12, wherein said composition further contains a buffer reagent.

14. A test composition according to claim 12, wherein said composition further contains a member selected from the group consisting of a surfactant, antiseptics and ascorbate oxidase.

15. A test composition according to claim 12, wherein said composition further contains an enzymatic hydrogen peroxide-producing system.

16. A test composition according to claim 12, wherein said system contains oxidase.

* * * * *